United States Patent
Melzer et al.

(10) Patent No.: US 11,147,909 B2
(45) Date of Patent: Oct. 19, 2021

(54) DIAPHRAGM VACUUM PUMP

(71) Applicant: MEDELA HOLDING AG, Baar (CH)

(72) Inventors: Martin Melzer, Cham (CH); Adrian Honegger, Lucerne (CH); Lukas Bannwart, Rotkreuz (CH)

(73) Assignee: MEDELA HOLDING AG, Baar (CH)

( * ) Notice: Subject to any disclaimer, the term of this patent is extended or adjusted under 35 U.S.C. 154(b) by 305 days.

(21) Appl. No.: 16/099,579

(22) PCT Filed: May 4, 2017

(86) PCT No.: PCT/EP2017/060639
§ 371 (c)(1),
(2) Date: Nov. 7, 2018

(87) PCT Pub. No.: WO2017/194383
PCT Pub. Date: Nov. 16, 2017

(65) Prior Publication Data
US 2019/0184073 A1    Jun. 20, 2019

(30) Foreign Application Priority Data
May 11, 2016  (EP) ..................................... 16169148

(51) Int. Cl.
*A61M 1/00*   (2006.01)
*A61M 1/06*   (2006.01)
(Continued)

(52) U.S. Cl.
CPC ................ *A61M 1/82* (2021.05); *A61M 1/06* (2013.01); *A61M 1/75* (2021.05); *F04B 9/045* (2013.01);
(Continued)

(58) Field of Classification Search
CPC .... A61M 1/0072; A61M 1/0037; A61M 1/06; A61M 2202/0014; F04B 9/045; F04B 35/01; F04B 45/047
See application file for complete search history.

(56) References Cited

U.S. PATENT DOCUMENTS 5,776,098 A  *  7/1998  Silver .................... A61M 1/062
                                                        604/74
8,535,284 B2      9/2013  Ramella et al.
(Continued)

FOREIGN PATENT DOCUMENTS

DE    2608664 A1  *  9/1977  .......... F04B 11/0066
EP    0286792 A2    10/1988
(Continued)

OTHER PUBLICATIONS

International Search Report for International Application No. PCT/EP2017/060639, dated Jul. 24, 2017.

*Primary Examiner* — Amber R Stiles
(74) *Attorney, Agent, or Firm* — Marshall, Gerstein & Borun LLP

(57) ABSTRACT

A diaphragm vacuum pump has a pump chamber, a vacuum diaphragm for generating an underpressure in the pump chamber, an electric motor (1) with a motor shaft, a gear and a connecting element. The gear converts a rotational movement of the motor shaft into a cyclical, approximately linear forward and rearward movement of the connecting element, as a result of which the connecting element effects a cyclical movement of the vacuum diaphragm. The rearward movement of the connecting element per cycle is effected by a first rotation angle of the motor shaft which, on account of the gear, is not of the same magnitude as a second rotation angle of the motor shaft, wherein the second rotation angle effects the forward movement of the connecting element per (Continued)

cycle. The diaphragm vacuum pump according to the invention can be designed such that it is small and quiet and yet provides optimal power.

22 Claims, 8 Drawing Sheets

(51) Int. Cl.
  *F04B 9/04* (2006.01)
  *F04B 35/01* (2006.01)
  *F04B 45/047* (2006.01)
(52) U.S. Cl.
  CPC ............ *F04B 35/01* (2013.01); *F04B 45/047* (2013.01); *A61M 2202/0014* (2013.01)

(56) References Cited

U.S. PATENT DOCUMENTS

| | | | |
|---|---|---|---|
| 2005/0228342 A1* | 10/2005 | Yuen | A61M 1/0029 604/74 |
| 2013/0061744 A1 | 3/2013 | Celotta et al. | |
| 2015/0354556 A1* | 12/2015 | Fong | F04B 53/16 417/374 |

FOREIGN PATENT DOCUMENTS

| | | | | |
|---|---|---|---|---|
| EP | 0456387 A1 * | 11/1991 | ............ | F04B 43/082 |
| WO | WO-93/03295 A1 | 2/1993 | | |
| WO | WO-2002/17992 A1 | 3/2002 | | |
| WO | WO-2011/035447 A1 | 3/2011 | | |

\* cited by examiner

DIAPHRAGM VACUUM PUMP

CROSS-REFERENCE TO RELATED APPLICATION

The present application is the US national phase of International Application No. PCT/EP2017/060639, filed May 4, 2017, which claims priority to European Application No. 16169148.0 filed May 11, 2016. The priority, EP 16169148.0, is hereby incorporated by reference in its entirety.

TECHNICAL FIELD

The present invention relates to a diaphragm vacuum pump. It relates in particular to medical suction pumps such as are used, for example, in breastpump units for expressing human breastmilk or for drainage pump units, in particular for thorax drainage, wound drainage or the aspiration of other bodily fluids or body fat.

PRIOR ART

Medical suction pumps, in particular breastpumps and drainage pumps, require a certain motor size in order to be able to provide sufficient power. This is a disadvantage particularly in the design of pumps that are portable during use, since the electric motors largely determine the weight of the pump units and, in addition, require a corresponding amount of space. Suction pumps of this kind are also relatively loud and disturb the mother and those around her and also the patient and the medical personnel.

U.S. Pat. No. 5,776,098 discloses a breastpump with an electric motor which, with the aid of an eccentriccam, converts a rotational movement of the motor shaft into a linear movement of a connecting or driving rod. The connecting rod is connected to a vacuum diaphragm, which generates an underpressure in a vacuum chamber. It is true that this pump has proven useful in practice. However, as has been mentioned above, a disadvantage is that it requires a powerful motor, since the torque profile on the motor has a relatively large peak.

A further breastpump, in which the vacuum diaphragm serves at the same time as a means for delivery of the breastmilk that is to be expressed, is disclosed in WO 2011/035447.

WO 2002/17992 and U.S. Pat. No. 8,535,284 disclose drainage pumps.

WO 93/03295 A1 and EP 0 456 387 A1 disclose peristaltic pumps which serve to administer a medicament and which use cam discs.

The prior art furthermore discloses multi-bar linkage systems, in particular four-bar linkage systems. For example, the Chebyshev lambda mechanism is a four-bar linkage which converts a rotational movement into an approximately rectilinear movement with an almost constant speed in a direction of movement.

DISCLOSURE OF THE INVENTION

It is therefore an object of the invention to make available a diaphragm vacuum pump that can be made small, light and cost-effective.

The diaphragm vacuum pump according to the invention has a pump chamber, a vacuum diaphragm for generating an underpressure in the pump chamber, an electric motor with a motor shaft, a gear and a connecting element. The gear converts a rotational movement of the motor shaft into a cyclical, approximately linear forward and rearward movement of the connecting element, as a result of which the connecting element effects a cyclical movement of the vacuum diaphragm. According to the invention, the rearward movement of the connecting element per cycle is effected by a first rotation angle of the motor shaft which, on account of the gear, is not of the same magnitude as a second rotation angle of the motor shaft, wherein the second rotation angle effects the forward movement of the connecting element per cycle.

This diaphragm vacuum pump is preferably suitable as a medical suction pump, in particular as an assembly in a breastpump unit or in a drainage pump unit. It is suitable in particular for use in pump units that are operated by battery.

A range of more than 180° of the rotational movement of the motor shaft, i.e. of the drive shaft, is used for one direction of movement. In this way, the load moment, i.e. the torque on the motor, for this direction of movement can be distributed over a relatively large angle range. Torque peaks, and therefore also load peaks, can thus be reduced. Preferably, this direction of movement is the suction stroke direction. The suction stroke direction, in which the diaphragm is drawn away from its starting position and from the wall of the pump chamber, is referred to here as the rearward direction. Therefore, "forward", as used in the text, is the area of the pump chamber, and "rearward" is the area of the end of the connecting element at a distance from the pump diaphragm.

According to the invention, it is thus possible to use smaller and less powerful but also quieter motors than in the eccentric crankshaft mechanism mentioned at the outset.

By contrast, if the same motor type as in an eccentric crankshaft mechanism is used, then the efficiency or power is increased.

By suitable choice of the motor, it is thus possible to find an optimum between the size, power and noise level of the pump.

It is moreover advantageous that the diaphragm is operated by a linear or an at least approximately linear movement. This protects the diaphragm and minimizes its wear.

It is not only the use of less powerful motors that reduces the noise level, but also the slowing down of the diaphragm movement in the suction stroke direction, which is occasioned by the longer travel of the connecting element in this suction stroke direction. By virtue of this slowing-down of the diaphragm movement, the pulsation of the delivery medium, usually air, is reduced.

A movement cycle of the connecting element and of the vacuum diaphragm usually corresponds to a rotational movement of the motor shaft about a total angle of 360°.

The rearward movement of the connecting element preferably defines the pump stroke which generates the vacuum in the vacuum chamber, wherein the first rotation angle assigned to this rearward movement is greater than the second rotation angle. In this way, the load can be distributed across a greater time interval and the load peak is minimized.

Preferably, the first rotation angle is greater than 180°, wherein it is preferably 200° to 300° and more preferably 240° to 270°. Preferably, ⅔ up to ¾ of the revolution of the motor shaft is used for the rearward movement or the pump stroke movement. This pump stroke movement therefore takes place preferably considerably more slowly than the opposite movement.

Preferably, the second rotation angle is smaller than 180°, wherein it is preferably 60° to 160° and more preferably 90° to 120°. Preferably, only ⅓ to ¼ of the revolution of the motor shaft is used for the opposite movement of the suction stroke. This opposite movement accordingly takes place more quickly than the suction stroke movement.

Preferably, the torque on the motor shaft for the rearward movement of the connecting element is distributed across an angle of greater than 180°. This distributes the torque on the motor across a greater range. High torque peaks are avoided.

The abovementioned features can be obtained with different gears. In a preferred embodiment, the gear is a cam disc gear which has a cam disc that deviates from a circle shape and that rotates during the operation of the diaphragm vacuum pump. Depending on the shape of the cam disc, it is possible to obtain a torque on the motor that remains approximately constant during the rearward movement. The movement of the connecting element can be effected linearly.

Preferably, in this case, the connecting element is a connecting rod which with a first end is connected to the vacuum diaphragm and which with a second end is mounted on the cam disc. Moreover, a guide means is present which guides the connecting rod in the approximately linear, preferably exactly linear, movement.

The cam disc can be made from metal, a coated metal, a ceramic-plastic composite, a coated ceramic, a metal-plastic composite or from other materials. It is preferably produced from plastic, in particular from a polymer. Moreover, the gear can be produced easily and cost-effectively and with a low weight.

In another embodiment, the gear is a multi-bar linkage, preferably a four-bar linkage. It is preferably designed as a Chebyshev lambda mechanism. The connecting element preferably forms a link member of the gear. Preferably, the connecting element is moved on an approximately straight line in the suction stroke direction, i.e. in the rearward direction, with constant speed. The movement is quicker in the opposite direction.

The multi-bar linkage can have various configurations. For example, it can have several link members that are held pivotably relative to one another but are otherwise independent of one another. The links, which define the pivot shafts, are in this case preferably roller bearings or ball bearings.

However, several of the link members or all of the link members can also be designed in one piece. In this case, the pivot shafts are preferably formed as film hinges, preferably by thinning of material. The gear is preferably formed in one piece with the connecting element. A one-piece design of this kind requires relatively little space and material and is also cost-effective in production. The multi-bar linkage can be made from the same materials as have already been mentioned. It is preferably made from metal or plastic or from a combination thereof. The one-piece configurations are preferably produced from plastic, in particular from a polymer.

The diaphragm vacuum pump according to the invention permits a relatively uniform and reduced loading of the electric motor, low-vibration and low-noise operation, and a cost-effective and compact format. The degree of efficiency can also be enhanced. Such diaphragm vacuum pumps can be made in all sizes. They are particularly suitable for relatively small battery-operated suction pump units that are also designed to be portable during use, of the kind already mentioned by way of example at the outset.

Further embodiments are set forth in the dependent claims.

BRIEF DESCRIPTION OF THE DRAWINGS

Preferred embodiments of the invention are described below with reference to the drawings, which serve only for explanatory purposes and are not to be interpreted as limiting the invention. In the drawings.

Identical parts are provided with identical reference signs.

DESCRIPTION OF PREFERRED EMBODIMENTS

Figure 1:
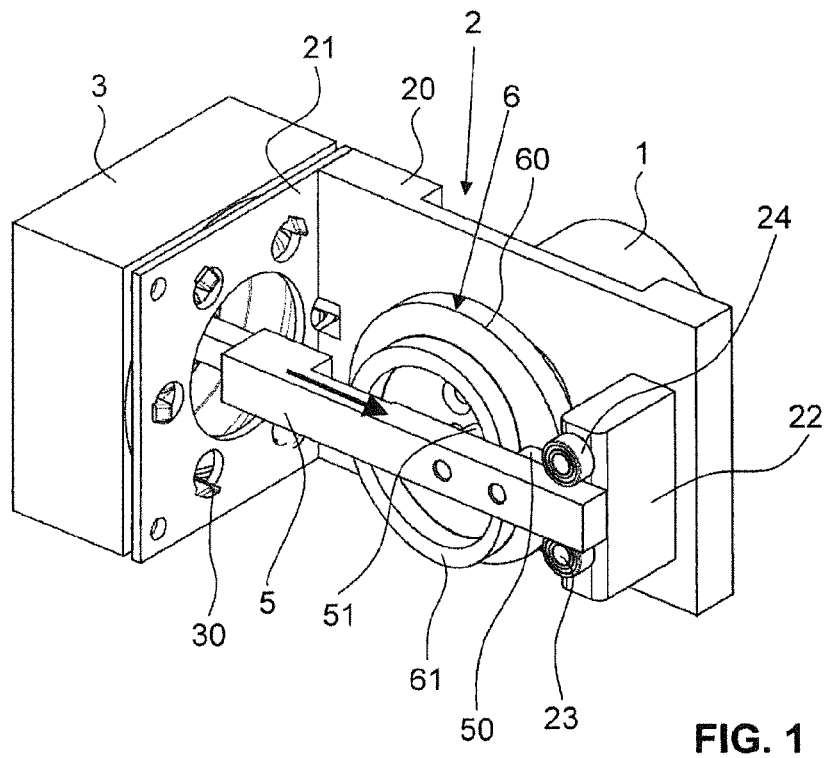
FIG. 1 shows a perspective view of a diaphragm vacuum pump according to the invention in a first embodiment.
Figure 2:
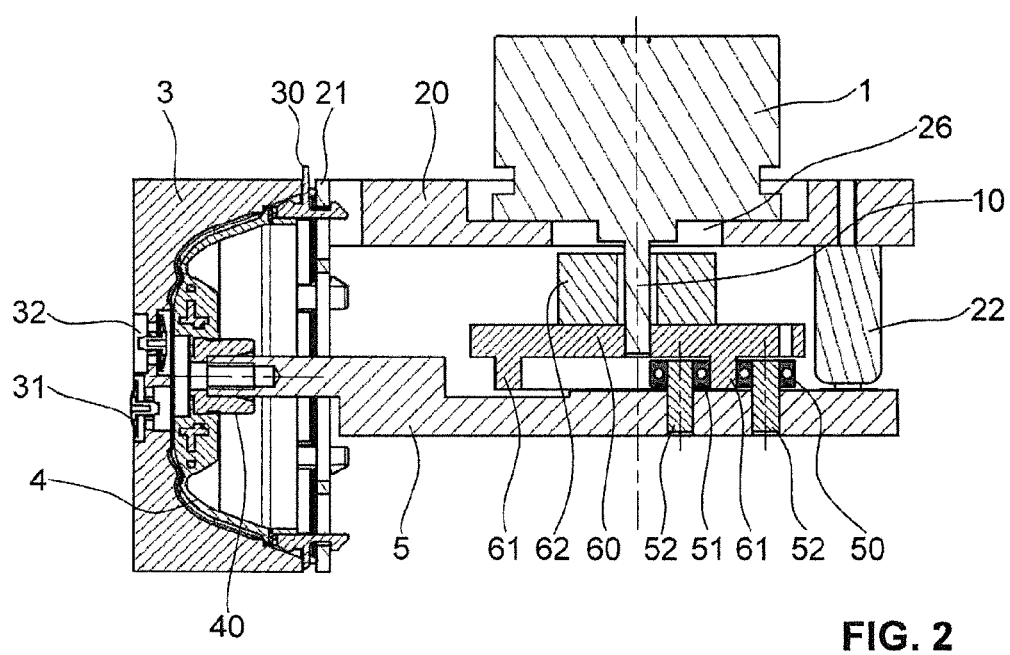
FIG. 2 shows a first longitudinal section through the pump according to FIG. 1.
Figure 3:
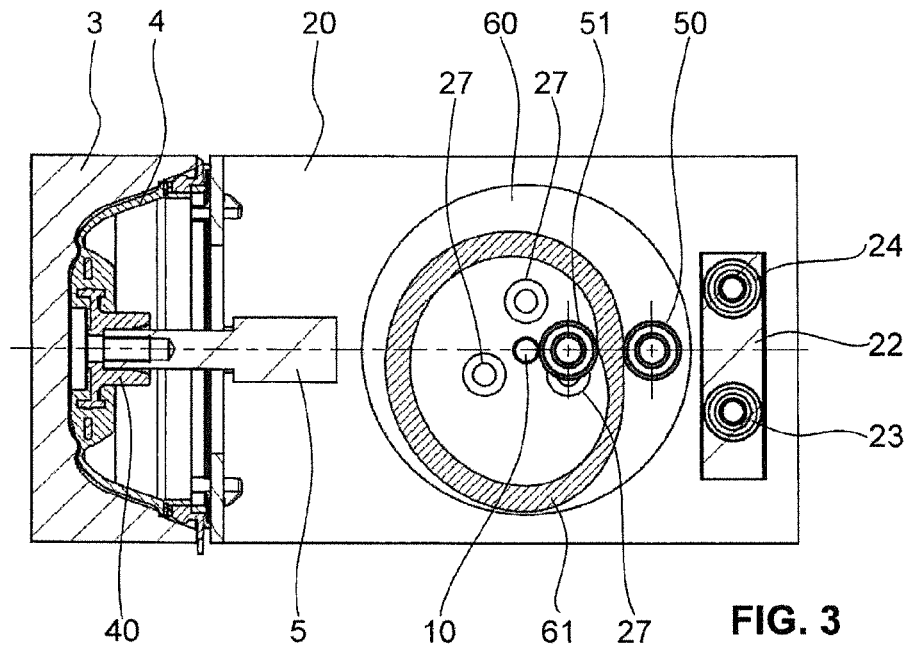
FIG. 3 shows a second longitudinal section through the pump according to FIG. 1.
Figure 4:
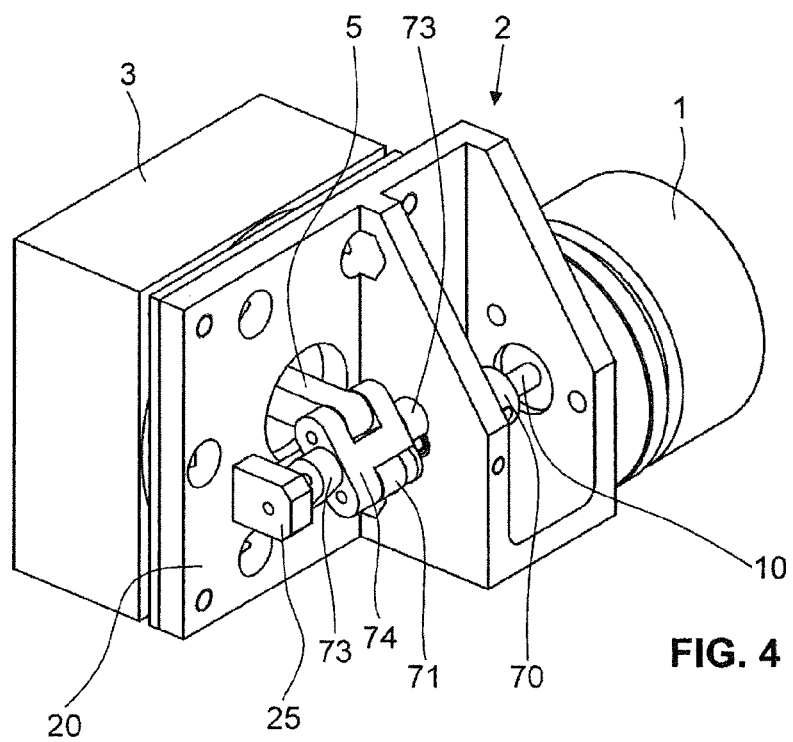
FIG. 4 shows a perspective view of a diaphragm vacuum pump according to the invention in a second embodiment.
Figure 5:
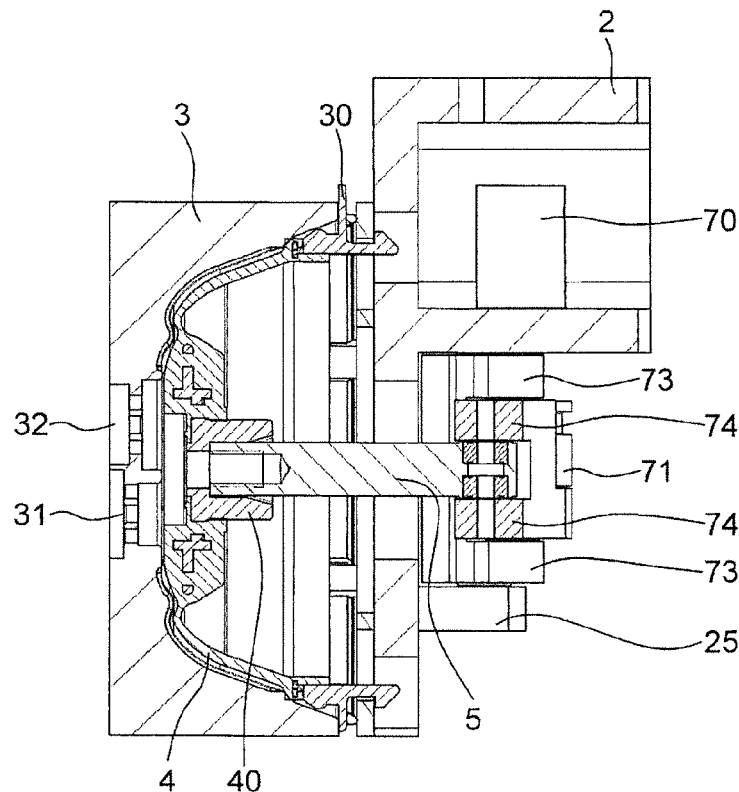
FIG. 5 shows a cross section through the pump according to FIG. 4.

FIGS. 1 to 3 show a first illustrative embodiment of the diaphragm vacuum pump according to the invention. This diaphragm vacuum pump has an electric motor 1. This electric motor 1 is held in a retainer 2 with a base plate 20. An electronics system for controlling the motor, a housing for receiving the elements shown, and operating means such as switches and rotary buttons for actuating the pump are not shown. The form and design of the retainer 2 are to be understood only as an example. Other forms and types of fastening of the individual elements of the pump, in particular of the motor and also of the pump chamber 3 and connecting element 5 described below, are also possible.

The electric motor 1 has a drive shaft, here called the motor shaft 10. The motor shaft 10 passes unimpeded through a through-opening in the base plate 20. The motor shaft 10 is fixedly connected to a cam disc gear 6. The gear 6 has a coupling element 62, which connects the rest of the gear to the motor shaft 10. The motor shaft 10 passes through the base plate 20 in a manner spaced apart from the latter and unimpeded. The free end of the motor shaft is fixedly connected to the base disc 60 likewise connected to the coupling element 62, such that, together with the coupling element 62, the base disc 60 rotates with the motor shaft 10. The base disc 60 is preferably connected at its centre to the motor shaft 10. The fastening holes for the connection to the coupling element 62 are provided with reference sign 27.

A protruding cam ring 61 is arranged on the base disc 60. Base disc 60 and cam ring 61 together form the cam disc. The cam ring 61 can be fastened to the base disc 60, i.e. can be a separate component, or it can be formed in one piece with the base disc 60. The latter option is preferred. As can be seen clearly in FIG. 3, the cam ring 61 has a shape deviating from a round circle. Moreover, it preferably has a changing wall thickness, as can likewise be seen clearly in FIG. 3. The shape corresponds in the broadest sense to a polynomial describing spiral segments. The wall thickness of the cam ring 61 varies such that driver rollers 50, 51, described below, bear free of play at each rotation angle.

As can best be seen in FIG. 1, a connecting element 5 is present which connects the gear 6 and thus the motor 1 to a pump diaphragm or vacuum diaphragm 4. The vacuum diaphragm 4 is arranged in a vacuum chamber 3, wherein the vacuum diaphragm 4 forms the movable rear wall of the vacuum chamber 3. A cover plate 21 of the retainer 2 is likewise fastened in this rear area. The corresponding fixing elements, here latching hooks, bear the reference sign 30.

Figure 6:
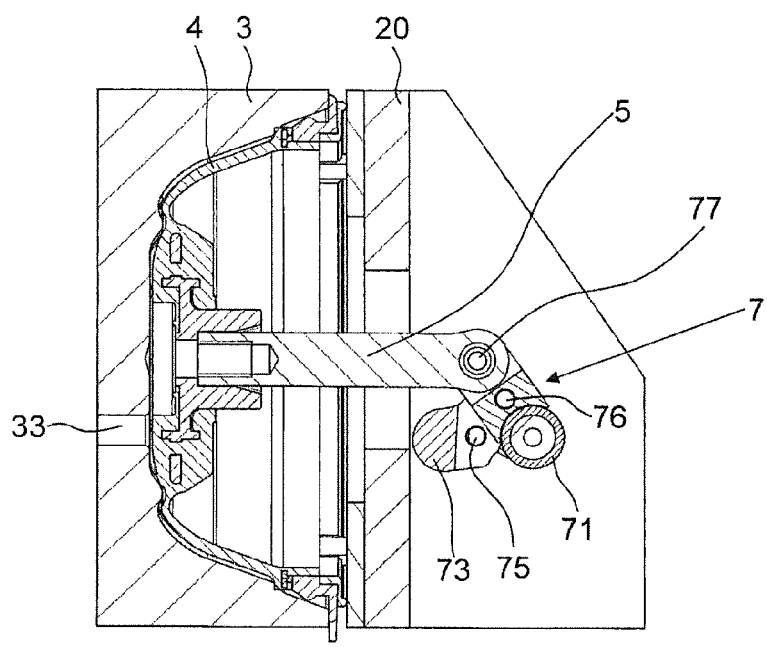
FIG. 6 shows a longitudinal section through the pump according to FIG. 4.
Figure 7:
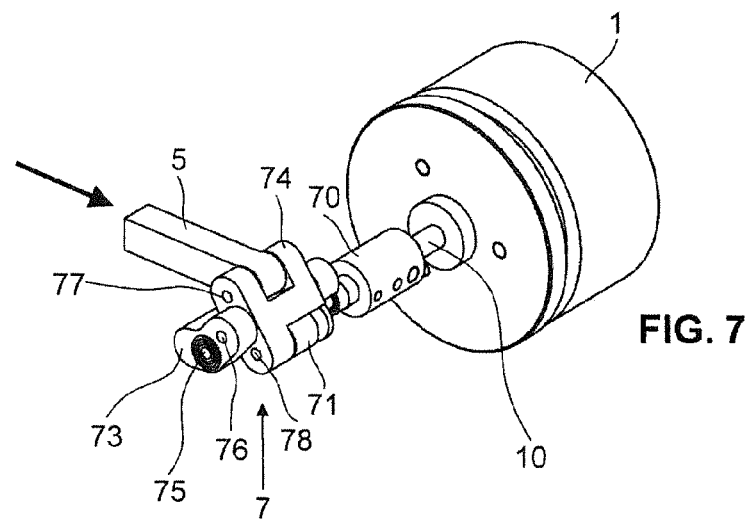
FIG. 7 shows a perspective view of the gear with motor and connecting element according to FIG. 4.
Figure 8:
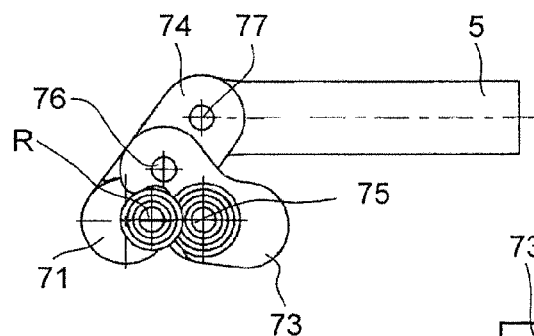
FIG. 8 shows a first side view of the unit according to FIG. 7.
Figure 9:
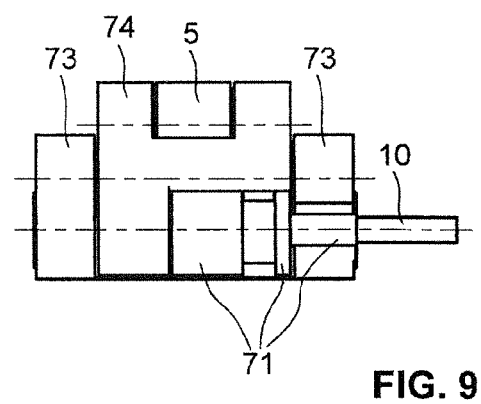
FIG. 9 shows a view of the unit according to FIG. 7 from behind.
Figure 10:
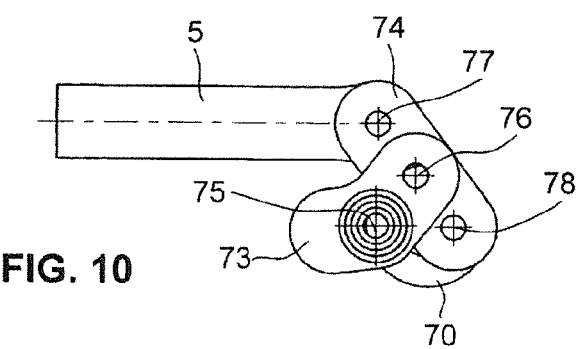
FIG. 10 shows a second side view of the unit according to FIG. 7.
Figure 11:
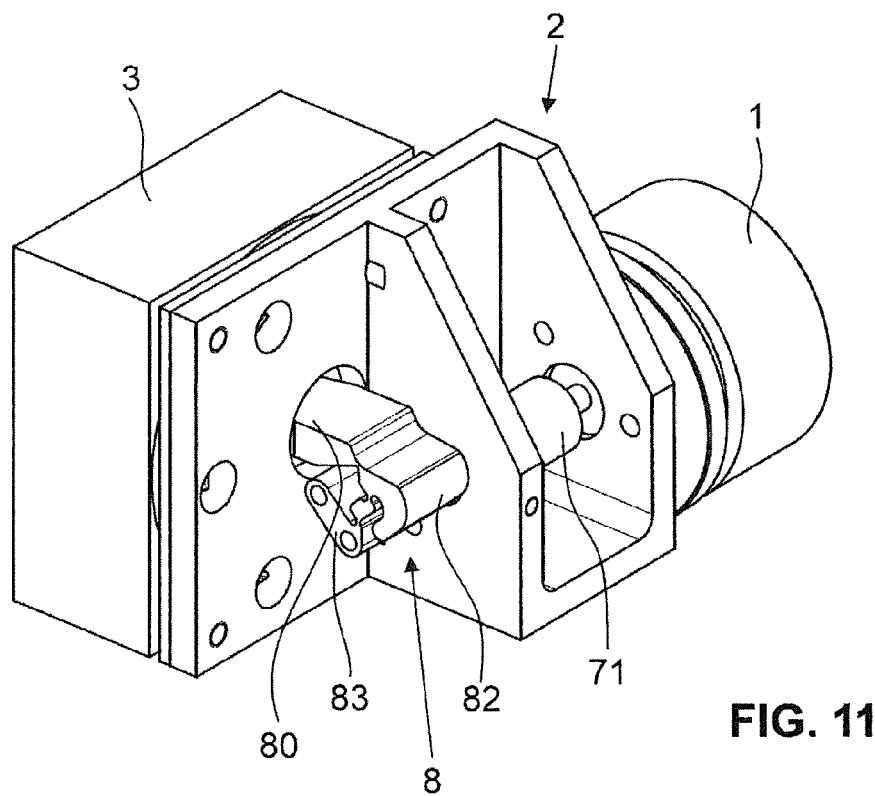
FIG. 11 shows a perspective view of a diaphragm vacuum pump according to the invention in a third embodiment.
Figure 12:
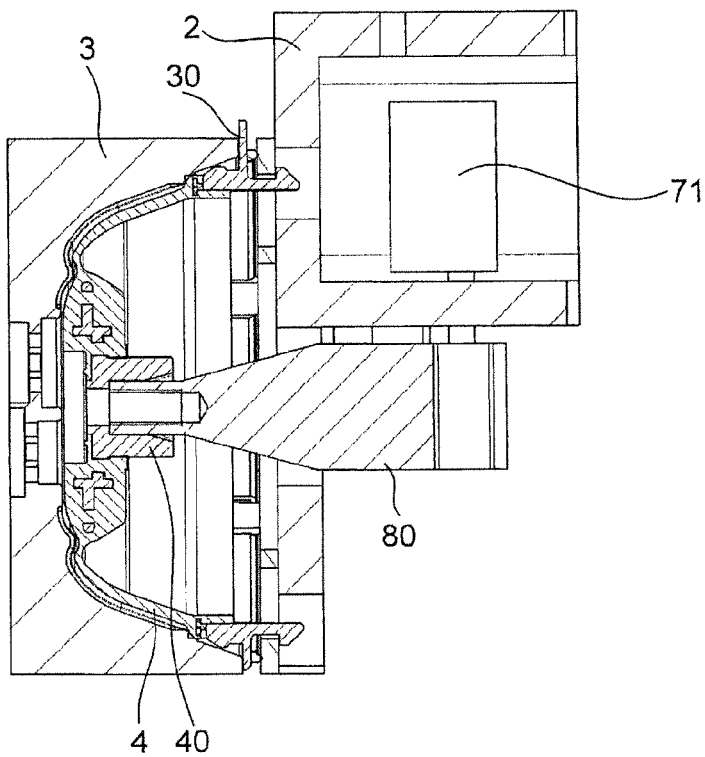
FIG. 12 shows a cross section through the pump according to FIG. 11.
Figure 13:
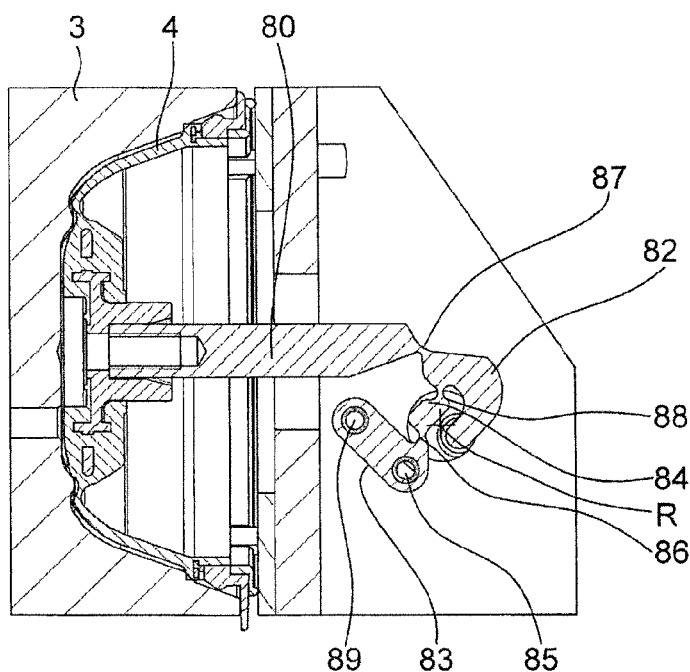
FIG. 13 shows a longitudinal section through the pump according to FIG. 11.
Figure 14:
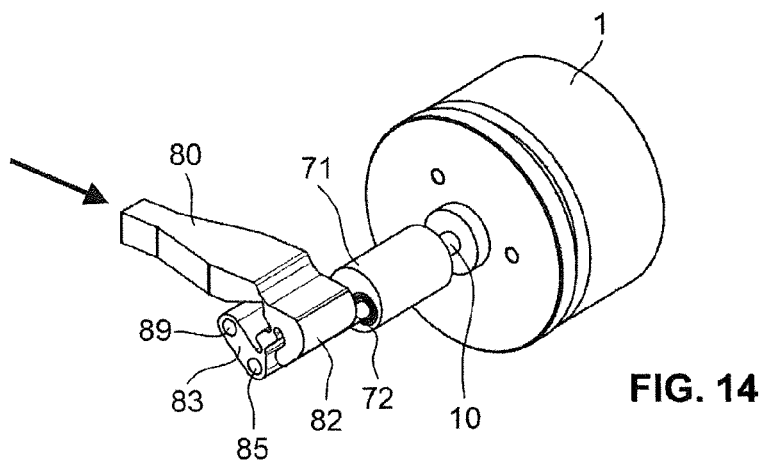
FIG. 14 shows a perspective view of the gear with motor and connecting element according to FIG. 11.
Figure 15:
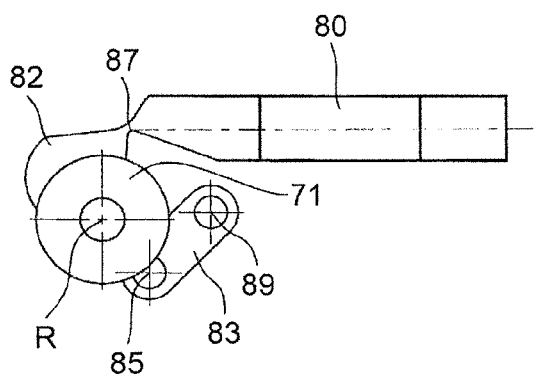
FIG. 15 shows a first side view of the unit according to FIG. 11.
Figure 16:
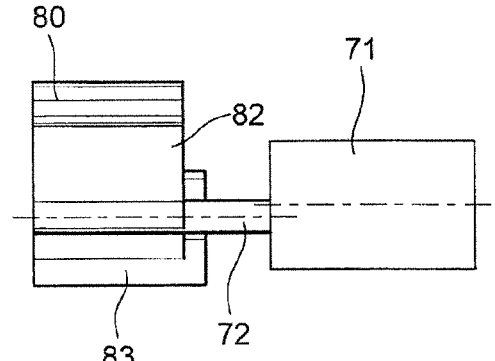
FIG. 16 shows a view of the unit according to FIG. 11 from behind.
Figure 17:
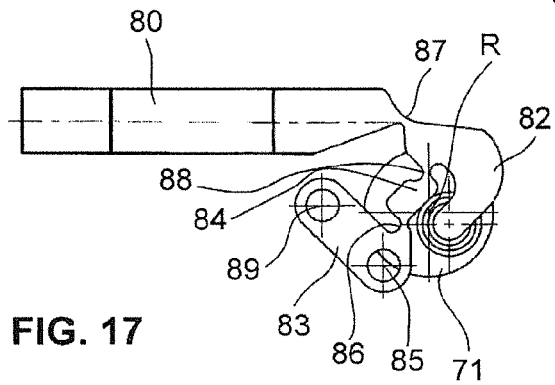
FIG. 17 shows a second side view of the unit according to FIG. 11.

The pump chamber 3 also preferably comprises an inlet valve 32 and an outlet valve 31 to allow air into and out of the vacuum chamber 3. A vacuum port for connection to a suction line or a suction cap, e.g. a breastshield, is not visible in FIGS. 1 to 3. In FIG. 6, it is provided with reference sign 33. This pump chamber 3 with vacuum diaphragm 4 has the customary shape and is not described in any more detail below.

The vacuum diaphragm 4 has a coupling element 40, for example a cylindrical socket, in which an end of the connecting element 5 is held fixed.

A second end of the bar-shaped or rod-shaped connecting element 5 is held in a linearly displaceable manner in a linear guide 22 of the retainer 2. For this purpose, the linear guide 22 has a pair of rollers with a first guide roller 23 and a second guide roller 24. These rollers are arranged above and below the connecting element 5 and clamp the latter, such that the connecting element 5 is guided through between them.

A first driver roller 50 and second driver roller 51 are fastened on the connecting element 5, are directed with their rotation shafts towards the cam ring 61 and bear the latter between them. The fastening is provided, for example, by means of fastening pins 52 which fix the driver rollers 50, 51 rotatably on the connecting rod 5.

During rotation of the motor shaft 10, the base disc 60 thus rotates with the cam ring 61. The driver rollers 50, 51 roll on the cam ring 61 and thus drive the connecting rod 5. The driver rollers 50, 51, together with the guide rollers 23, 24, have the effect that the connecting rod 5 is moved away from the pump chamber 3 in a linear rearward movement according to the movement of the cam ring 61 and draws the vacuum diaphragm 4 with it. The rearward movement is indicated by an arrow in the figures.

An underpressure exists in the pump chamber 3. Depending on the shape of the cam ring 61, the connecting rod 5 moves forwards again such that the vacuum diaphragm 4 can recover its starting position.

On account of the special shape of the cam ring 61, the connecting rod 5 needs longer for the rearward movement than for the forward movement. The rearward movement is slower than the movement in the opposite direction. Moreover, it requires a larger angle range of the rotation of the motor shaft 10 than does the forward movement.

Figure 18:
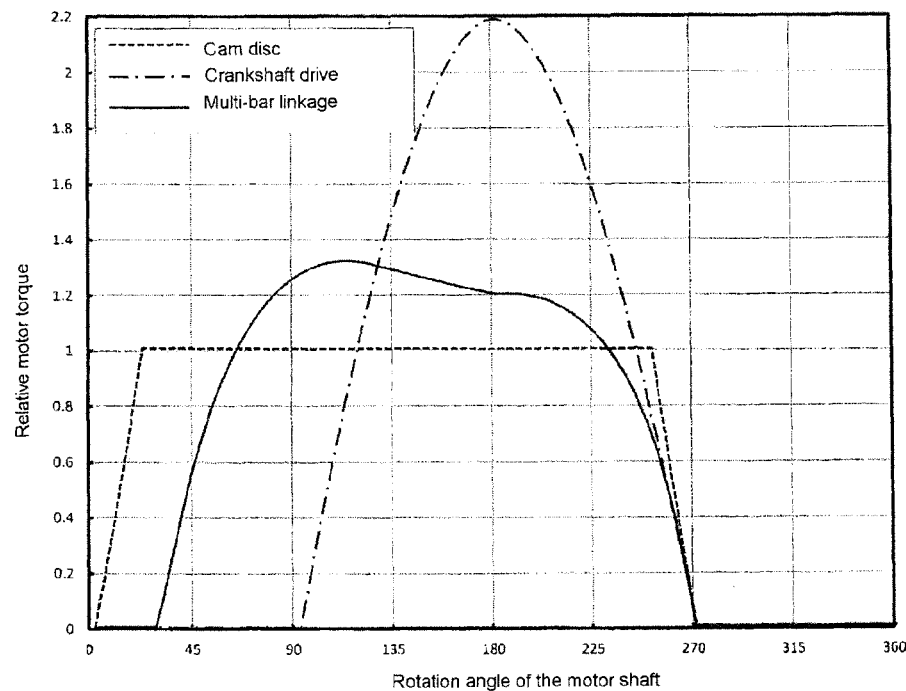
FIG. 18 shows a diagram illustrating the relative torque on the motor as a function of the rotation angle of the motor shaft.
Figure 19:
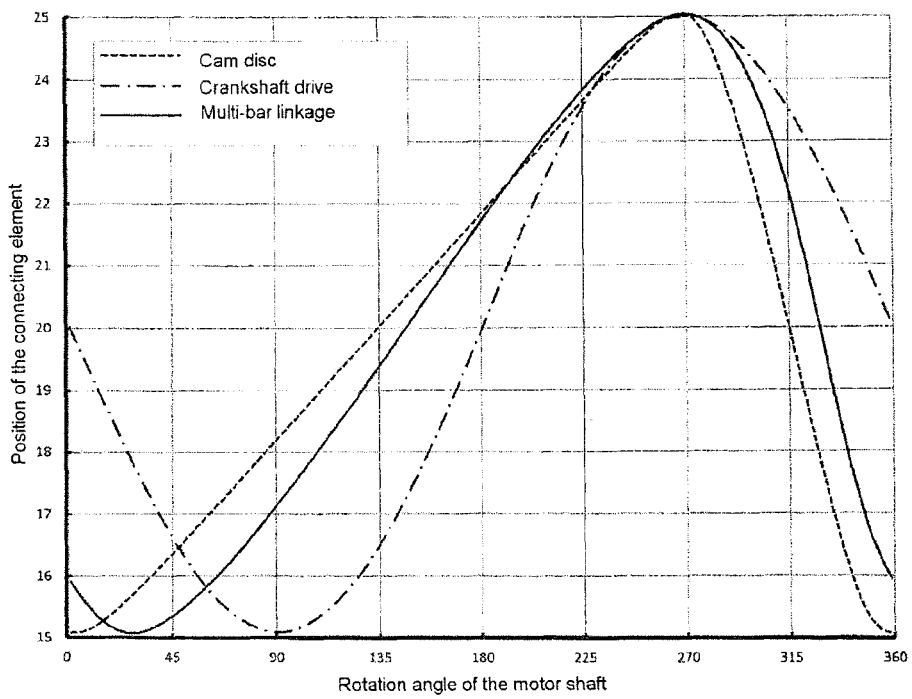
FIG. 19 shows a diagram illustrating the position of the connecting element as a function of the rotation angle of the motor shaft.

As can be seen in FIGS. 18 and 19, the connecting rod 5 requires a rotational movement of the motor shaft 10 from 0° to 270°, i.e. ¾ of the full revolution per cycle, in order to reach the position of maximum suction stroke. By contrast, the forward movement of the connecting rod 5 to the starting position of the vacuum diaphragm 4 requires 90°, i.e. ¼ of the full revolution of the motor shaft 10 per cycle. This can be seen in FIG. 19.

The torque to be applied, or the load moment on the motor shaft 10 or on the motor 1, is shown in FIG. 18. As can be seen there, the torque rises very rapidly at the start of the cycle and is then constant across an angle range of almost 270°, until it drops again with a strong negative slope upon completion of the rearward movement.

The comparison with the torque (likewise indicated) of a crankshaft drive shows that the torque peak present in the crankshaft drive, the square of which peak corresponds to the peak power, is now hugely minimized. As can be seen in FIGS. 18 and 19, the forward and rearward movements in the eccentric crankshaft drive are symmetrical, such that they each require an angle range of 180° and the drive rod is moved equally quickly in both directions.

FIGS. 18 and 19 likewise show the behaviour of a diaphragm vacuum pump according to the invention with a multi-bar linkage. Two variants thereof are described below. As can be seen in FIGS. 18 and 19, the rearward movement of the connecting element, i.e. the suction stroke, also extends here across an angle range that is much greater than 180°. It is ca. 250° in FIG. 18. The forward movement takes place more quickly and extends only across an angle range of ca. 110°. The movement of the connecting element 5 is approximately linear, although it does not necessarily have to be exactly linear. It will be seen in FIG. 19 that in this case too the peak loads and torque peaks are attenuated. The torque on the motor shaft 10 or on the motor 1 is approximately constant, but not so constant as in the use of the cam disc.

A first variant of a diaphragm vacuum pump with a multi-bar linkage 7 is shown in FIGS. 4 to 10. The electric motor 1 is held in the retainer 2, wherein the motor shaft 10 passes unimpeded through the retainer 2. The motor shaft 10 is connected to an eccentric element 71 for conjoint rotation via a coupling element 70. The rotation axis of the motor shaft is provided with reference sign R in the figures.

A fork-shaped first link member 73 engages around the eccentric element 71, without being directly connected thereto. At one end, it is mounted pivotably on a bearing 25 of the retainer 2. This bearing forms the first pivot shaft 75. The first link member 73 is pivotably connected to a second link member 74 via a second pivot shaft 76. Moreover, the second link member 74 is pivotably connected to the connecting rod 5 via a third pivot shaft 77 and to the eccentric element 71 via a fourth pivot shaft 78. The connecting rod 5 forms a third link member.

These connections can be seen clearly in an overview of FIGS. 7 to 10. In this example, the pivot shafts are preferably formed by ball bearings or roller bearings.

These connections and the design and arrangement of the individual link members have the effect that the rotational movement is converted into an approximately linear or an exactly linear movement of the connecting rod 5, wherein the rearward movement, i.e. the suction stroke movement, for deflecting the vacuum diaphragm 4 takes place across a larger angle range and more slowly than the forward movement. The positions of the connecting rod 5 and the torque across the motor 1 are as explained with reference to FIGS. 18 and 19 and have already been described in the text above.

In the second variant of the multi-bar linkage according to FIGS. 11 to 17, the gear including the connecting rod is formed in one piece. It is preferably made from plastic or metal. Motor 1, motor shaft 10, pump chamber 3, retainer 2 and eccentric element 71 are designed in the manner mentioned above. Here, an eccentric shaft 72 of the eccentric element 71 passes unimpeded through the retainer 2 and rotates about the rotation axis R.

The gear is designed as a film-hinge linkage 8. It has a bar-shaped or rod-shaped connecting arm 80, which replaces the connecting rod 5 described above. Moreover, the gear 8 comprises a first link member 82, a second link member 83, a third link member 84 and also a first pivot shaft 86, a second pivot shaft 87 and a third pivot shaft 88, which interconnect the individual link members and the connecting arm, as already described above with reference to the first variant. Reference signs 85 and 89 show a first and a second fastening point of the connecting arm 80 to the retainer 2. The first, second and third pivot shafts 86, 87, 88 are designed as film hinges, preferably by thinning of material. The first link member 82 preferably has an arc-shaped cross section and merges via the second pivot shaft 87 into the connecting arm 80. By way of the third pivot shaft 88, it moreover merges into the third link member 84. The third link member 84 has an approximately rectangular cross section, wherein the third pivot shaft 88 is arranged at a first corner thereof. At a diametrically opposite corner lies the first pivot shaft 86, which connects the third link member 84 to the second link member 83. The cross section of the second link member 83 has a rounded rectangular shape but is many times larger than the third link member 83 and has approximately the same cross-sectional area as, or a slightly greater cross-sectional area than, the first link member 82. The connecting arm 80 again forms the fourth link member of the gear 8.

In this variant too, the rotational movement of the motor shaft 10 has the effect that the connecting arm 80 moves approximately or exactly linearly and, as in the first variant, it has an approximately uniform but slow speed in the rearward movement and, for the full suction stroke, it requires a greater angle range of the rotational movement than is the case for the forward movement. The information on this can again be found in FIGS. 18 and 19 and in the above description.

The diaphragm vacuum pump according to the invention can thus be designed such that it is quiet and yet provides optimal power.

LIST OF REFERENCE SIGNS

| | |
|---|---|
| 1 | electric motor |
| 10 | motor shaft |
| 2 | retainer |
| 20 | base plate |
| 21 | cover plate |
| 22 | linear guide |
| 23 | first guide roller |
| 24 | second guide roller |
| 25 | bearing |
| 26 | through-opening |
| 27 | fastening holes |
| 3 | vacuum chamber |
| 30 | fixing element |
| 31 | outlet valve |

-continued

LIST OF REFERENCE SIGNS

| | |
|---|---|
| 32 | inlet valve |
| 33 | pressure sensor attachment |
| 4 | pump diaphragm |
| 40 | coupling element |
| 5 | connecting rod |
| 50 | first driver roller |
| 51 | second driver roller |
| 52 | fastening pin |
| 6 | cam disc gear |
| 60 | base disc |
| 61 | cam ring |
| 62 | coupling element |
| 7 | multi-bar linkage |
| 70 | coupling element |
| 71 | eccentric element |
| 72 | eccentric shaft |
| 73 | first link member |
| 74 | second link member |
| 75 | first pivot shaft |
| 76 | second pivot shaft |
| 77 | third pivot shaft |
| 78 | fourth pivot shaft |
| 8 | film-hinge linkage |
| 80 | connecting arm |
| 82 | first link member |
| 83 | second link member |
| 84 | third link member |
| 85 | first fastening point |
| 86 | first pivot shaft |
| 87 | second pivot shaft |
| 88 | third pivot shaft |
| 89 | second fastening point |
| R | rotation axis |

The invention claimed is:

1. A diaphragm vacuum pump with a pump chamber, a vacuum diaphragm for generating an underpressure in the pump chamber, an electric motor with a motor shaft, a gear and a connecting element, wherein the gear converts a rotational movement of the motor shaft into a cyclical, approximately linear forward and rearward movement of the connecting element, as a result of which the connecting element effects a cyclical movement of the vacuum diaphragm, wherein the rearward movement of the connecting element per cycle is effected by a first rotation angle of the motor shaft which, on account of the gear, is not of the same magnitude as a second rotation angle of the motor shaft, wherein the second rotation angle effects the forward movement of the connecting element per cycle, wherein the rearward movement of the connecting element defines a pump stroke of the cycle that generates the underpressure in the pump chamber, and wherein the first rotation angle is greater than the second rotation angle.

2. The diaphragm vacuum pump according to claim 1, wherein a movement cycle of the connecting element and of the vacuum diaphragm corresponds to a rotational movement of the motor shaft about a total angle of 360°.

3. The diaphragm vacuum pump according to claim 1, wherein the first rotation angle is greater than 180°.

4. The diaphragm vacuum pump according to claim 3, wherein the first rotation angle is 200° to 300°.

5. The diaphragm vacuum pump according to claim 3, wherein the first rotation angle is 240° to 270°.

6. The diaphragm vacuum pump according to claim 1, wherein the second rotation angle is smaller than 180°.

7. The diaphragm vacuum pump according to claim 6, wherein the second rotation angle is 60° to 160°.

8. The diaphragm vacuum pump according to claim 6, wherein the second rotation angle is 90° to 120°.

9. The diaphragm vacuum pump according to claim 1, wherein the torque on the motor shaft for the rearward movement of the connecting element is distributed across an angle of greater than 180°.

10. The diaphragm vacuum pump according to claim 1, wherein the gear is a cam disc gear which has a cam disc that deviates from a circle shape and that rotates during the operation of the diaphragm vacuum pump.

11. The diaphragm vacuum pump according to claim 10, wherein the connecting element is a connecting rod which with a first end is connected to the vacuum diaphragm and which with a second end is mounted on the cam disc, and wherein a guide means is present which guides the connecting rod in the approximately linear movement.

12. The diaphragm vacuum pump according to claim 10, wherein at least the cam disc is made from plastic.

13. The diaphragm vacuum pump according to claim 10, wherein the connecting element is a connecting rod which with a first end is connected to the vacuum diaphragm and which with a second end is mounted on the cam disc, and wherein a guide means is present which guides the connecting rod in the linear movement.

14. The diaphragm vacuum pump according to claim 1, wherein the gear is a multi-bar linkage.

15. The diaphragm vacuum pump according to claim 14, wherein the connecting element forms a link member of the gear.

16. The diaphragm vacuum pump according to claim 14, wherein the multi-bar linkage has several link members held pivotably relative to one another.

17. The diaphragm vacuum pump according to claim 14, wherein the gear is designed in one piece, and wherein the pivot shafts are formed by film hinges.

18. The diaphragm vacuum pump according to claim 17, wherein the gear is formed in one piece together with the connecting element.

19. The diaphragm vacuum pump according to claim 14, wherein the gear is made from plastic.

20. The diaphragm vacuum pump according to claim 14, wherein the gear is a four-bar linkage.

21. The diaphragm vacuum pump according to claim 14, wherein the connecting element is made from plastic.

22. The diaphragm vacuum pump according to claim 14, wherein the gear and the connecting element are made from plastic.

* * * * *